United States Patent
Linington et al.

(10) Patent No.: US 9,290,474 B2
(45) Date of Patent: Mar. 22, 2016

(54) METHODS FOR MAKING AND USING NOVEL SEMI-SYNTHETIC SMALL MOLECULES FOR THE TREATMENT PARASITIC DISEASE

(71) Applicants: Roger R Linington, Santa Cruz, CA (US); Gabriel Navarro, Santa Cruz, CA (US); Khanitha Pudhom, Santa Cruz, CA (US); James McKerrow, Santa Cruz, CA (US)

(72) Inventors: Roger R Linington, Santa Cruz, CA (US); Gabriel Navarro, Santa Cruz, CA (US); Khanitha Pudhom, Santa Cruz, CA (US); James McKerrow, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/574,092

(22) Filed: Dec. 17, 2014

(65) Prior Publication Data
US 2015/0105453 A1   Apr. 16, 2015

Related U.S. Application Data

(62) Division of application No. 14/236,030, filed as application No. PCT/US2012/048743 on Jul. 28, 2012, now Pat. No. 8,946,455.

(60) Provisional application No. 61/513,027, filed on Jul. 29, 2011.

(51) Int. Cl.
| | |
|---|---|
| *C07D 319/02* | (2006.01) |
| *C07D 311/02* | (2006.01) |
| *C07D 405/12* | (2006.01) |
| *C07D 407/12* | (2006.01) |
| *C07D 409/12* | (2006.01) |
| *C07D 413/12* | (2006.01) |
| *C07D 417/12* | (2006.01) |

(52) U.S. Cl.
CPC ............ *C07D 319/02* (2013.01); *C07D 311/02* (2013.01); *C07D 405/12* (2013.01); *C07D 407/12* (2013.01); *C07D 409/12* (2013.01); *C07D 413/12* (2013.01); *C07D 417/12* (2013.01)

(58) Field of Classification Search
CPC .................................................... C07D 311/02
USPC ........................................................ 549/360
See application file for complete search history.

Primary Examiner — Nizal Chandrakumar
(74) Attorney, Agent, or Firm — Adam Warwick Bell; Matthew Rupert Kaser (57) ABSTRACT

Small molecule therapeutics for the treatment of parasitic diseases, in particular, semi-synthetic derivatives of the fungally-derived natural product merulin A for the treatment of African Sleeping Sickness.

3 Claims, 8 Drawing Sheets

Figure 1: Known antiparasitic agents against T. brucei.

Figure 2: A generic structure for the derivatized compounds of the invention

12           13

Figure 3: Structures of composition 12 and Composition 13

Figure 4 (also referred to as Scheme 1): Synthetic derivatization of merulin core Table 1. Available treatments for HAT

| Drug | Parasite Specificity | Stage Specificity | Limitations |
|---|---|---|---|
| Sumarin | rhodensiense | first-stage | Efficacy, parenteral |
| Malarsoprol | gambiense & rhodensiense | second-stage | Safety, parenteral |
| Pentamidine | gambiense | first-stage | Resistance, compliance, parenteral |
| Eflornithine | gambiense | second-stage | Cost, parenteral |

Figure 5 (also called Table 1): Available treatments for HAT

| Desirable | Acceptable : improvement to current S2 Tx |
|---|---|
| Effective against stage 1 and 2 | Effective against stage 2 |
| Broad Spectrum (gambiense and rhodesiense) | Efficacy against gambiense only |
| Clinical efficacy > 95% at 18 months follow up | Clinical efficacy no worse than current treatments |
| Effective in melarsoprol refractory patients | |
| <0.1% drug related mortality | 1% drug related mortality |
| Safe during pregnancy and for lactating women | |
| Formulation adapted to adults and children | |
| No monitoring for AEs | Weekly simple lab testing (field testing) |
| < 7 days p.o. once daily (DOT) | < 20 days p.o. (DOT) |
| < 7 days i.m. once daily | < 20 days i.m. |
| | < 5 days i.v. if no toxicity |
| Stability in Zone 4 for > 3 years | Stability in Zone 4 for > 12 months |
| Cidal | |
| Multitarget | Unique target (but not uptake via P2-transporter only) |
| < 30 € / course* (only drug cost) | < 100 €* / course |
| | < 200 €* / course ok if very good on other criteria |

Figure 6 (also called Table 2): DNDi target product profile.

| Parameters | Drug-Like | Merulin A | Merulin B | Merulin C | 12 |
|---|---|---|---|---|---|
| Molecular Weight | 400-450 | 254 | 284 | 282 | 364 |
| # of Rotable Bonds | 6 | 0 | 2 | 2 | 3 |
| H-Bond Acceptors | 4 | 4 | 4 | 5 | 4 |
| H-Bond Donors | 1-2 | 1 | 2 | 2 | 0 |
| cLogP | 4-4.5 | 2.13 | 1.37 | 1.37 | 4.41 |
| TPSA (Å2) | 70-80 | 75 | 58.92 | 91.37 | 71.06 |
| Aromatic Rings | 2-4 | 0 | 0 | 0 | 1 |

Figure 7 (also called Table 3): Comparison of pharmokinetic properties of drug-like compounds to natural products merulin A-C.

Figure 8 (also called Table 4) Synthetic library of Merulin analogues

| Structure | T. brucei IC50 (uM) | HeLa Cell IC50 (uM) | SI | Serum Stability Half-life (Hrs) | Structure | T. brucei IC50 (uM) | HeLa Cell IC50 (uM) | SI | Serum Stability Half-life (Hrs) |
|---|---|---|---|---|---|---|---|---|---|
| 16 | 0.06 | > 50 | > 833 | n.d. | 39 | 0.24 | > 50 | > 208 | 1.5 |
| 17 | 0.26 | 28 | 107 | 19 | 27 | 0.95 | > 50 | > 52 | 3 |
| 18 | > 30 | 40 | < 1 | 0 | 28 | 14 | > 50 | > 3 | 8 |
| 14 | 0.42 | > 50 | > 119 | 9.5 | 29 | 0.21 | 24 | 114 | 7 |
| 19 | 0.11 | 13 | 118 | 0 | 30 | 0.16 | 33 | 206 | 0 |
| 20 | 0.27 | 12 | 44 | 0 | 31 | 0.53 | 21 | 39 | 0 |

Figure 8 continued.

| Structure | | | | | Structure | | | | |
|---|---|---|---|---|---|---|---|---|---|
|  | 0.043 | 13 | 302 | n.d. |  | >200 | >50 | 0 | n.d. |
|  | 0.70 | >50 | 71 | 0 |  | 24 | >50 | >2 | 0 |
|  | 0.66 | 13 | 19 | 5 |  | 31 | 50 | >1 | 5 |
|  | 0.33 | 16 | 48 | 15 |  | 11 | 14 | 1 | 15 |
|  | 0.54 | 21 | 38 | 0 |  | 11 | 50 | 4 | 0 |
|  | 0.19 | >50 | >263 | 3.5 |  | 0.37 | 38 | 102 | 3.5 |
|  | 1.8 | >50 | >27 | 2 |  | >200 | >50 | 0 | 2 |

Figure 9: Merulin A and various substituent groups used to derivatize Merulin

US 9,290,474 B2

METHODS FOR MAKING AND USING NOVEL SEMI-SYNTHETIC SMALL MOLECULES FOR THE TREATMENT PARASITIC DISEASE

RELATION TO OTHER APPLICATIONS

The present invention is a divisional application of and claims the benefit of and priority to U.S. application Ser. No. 14/236,030 filed 29 Jan. 2014 titled "Novel semi-synthetic small molecules for the treatment parasitic disease" which application is incorporated by reference for all purposes. U.S. application Ser. No. 14/236,030 itself claims the benefit of and priority to U.S. application No. 61/513,027 filed 29 Jul. 2011 which application is incorporated by reference for all purposes.

GOVERNMENT SPONSORSHIP

This work was sponsored by US government grant NIH 1R56AI085177_01A1 (RGL), the Government has certain rights in the invention.

FIELD OF THE INVENTION

Small molecule therapeutics for the treatment of parasitic diseases, in particular, semi-synthetic derivatives of the fungally-derived natural compound Merulin A for the treatment of African Sleeping Sickness.

BACKGROUND

Human African Trypanosomiasis (HAT) is transmitted by the tsetse fly vector, *T. brucei gambiense* and *rhodensiense*, and if untreated, is lethal. Current treatments are poor. In particular, the side effects for the treatment of the second stage infection (CNS infection) are very serious. There is therefore an unmet need for the development of new approaches to the development of endoperoxide-containing compounds as lead compounds for HAT.

BRIEF DESCRIPTION OF THE INVENTION

The invention encompasses semi-synthetic derivatizations of the fungally-derived natural product, Merulin.

BRIEF DESCRIPTION OF THE FIGURES

FIG. 5: (also referred to as Table 1: Available treatments for HAT
FIG. 6: (also referred to as Table 2): DNDi target product profile.

DETAILED DESCRIPTION OF THE INVENTION

Semi-synthetic derivatization of the fungally-derived natural product merulin A (4) has led to the discovery of a new development candidate for the protozoan parasite *Trypanosoma brucei*, the causative agent of African sleeping sickness. This new compound exhibits low nanomolar activity against *T. brucei*, with minimal mammalian cell cytotoxicity. Creation of an initial SAR library based around the merulin scaffold revealed both key features required for activity, and a position suitable for further derivatization. Subsequent synthesis of a 20 ester analogue library, guided by the addition of acyl groups that improve the drug like properties of the merulin A core, resulted in the synthesis of compound 12 with an $IC_{50}$ of 56 nM, a selectivity index greater than 250-fold, and a serum stability half life of 15 hours.

Merulins A-C (4-6) are a new class of endoperoxide-containing natural products recently isolated in one of our laboratories, that can be isolated in high yield (>28 mg/L) from liquid fungal cultures. This compound class contains many inherent properties that give it a strong position to overcome the obstacles that have hampered previous attempts to develop endoperoxide-based treatments for HAT. We were therefore interested to explore the potential for these compounds to be developed as new lead compounds in this area. Isolated from a Meruliaceae endophytic fungus (Subkingdom Dikarya, Phylum Basidiomycota), merulin A was isolated at yields of 28 mg per liter. While the original isolation publication reported two additional analogues, two other recent studies have expanded the suite of merulin-like compounds to eight (other analogues renamed as talaperoxides A-D, and steperoxide A).

Figure 4:
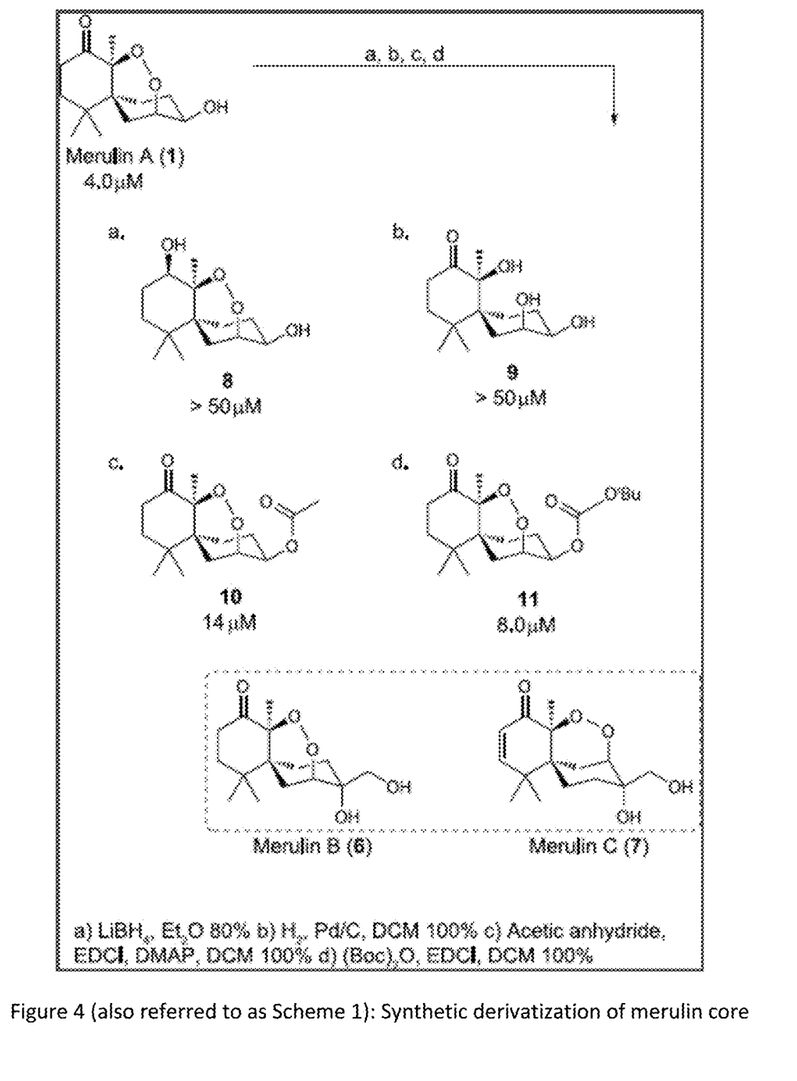
FIG. 4 (also referred to as Scheme 1): Synthetic derivatization of merulin core.
Figure 5:
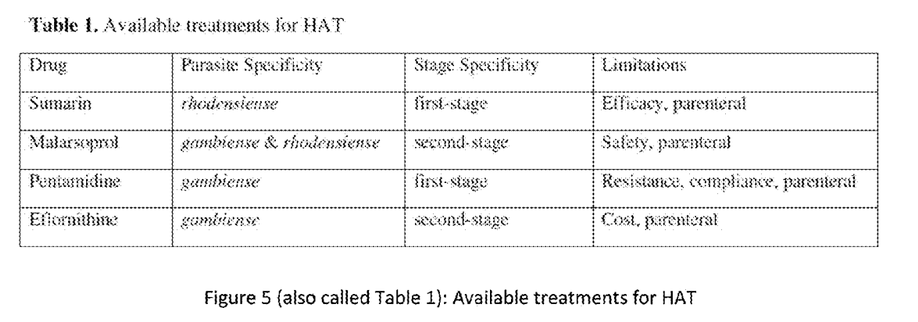
Figure 6:
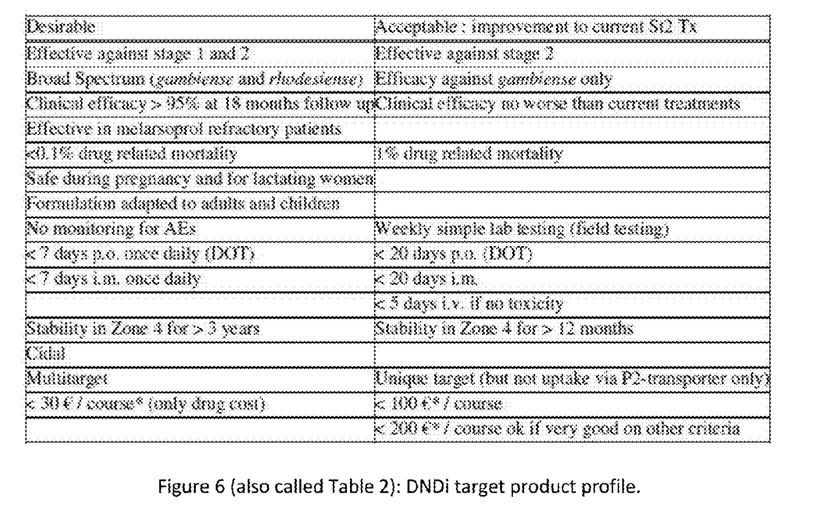
Figure 7:
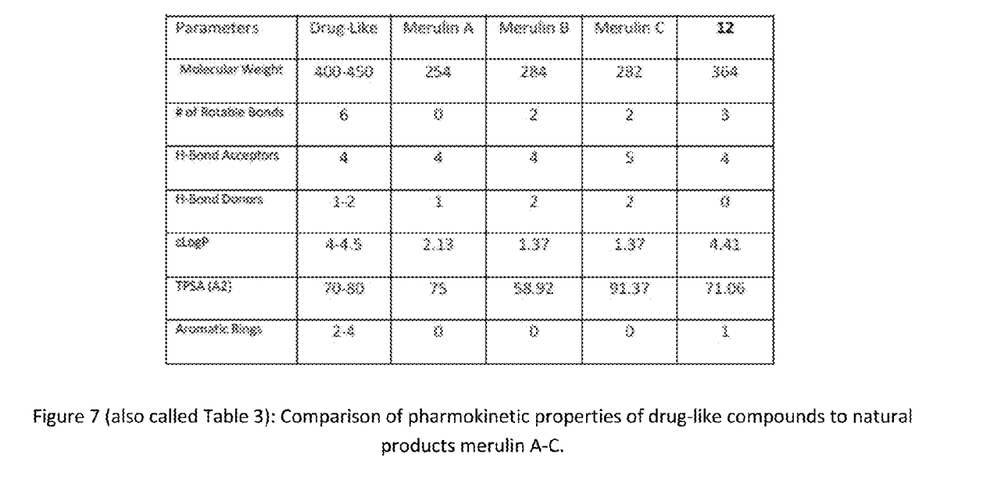
FIG. 7: (also referred to as Table 3): Comparison of pharmacokinetic properties of drug-like compounds to natural products merulin A-C.

Most of these merulin analogs, along with the parent compound merulin A, were reported as possessing moderate cytotoxicities against mammalian cell lines (10-30 µM), but were not tested for antiprotozoal activity. Initial screening of merulins A-C against *T. brucei* brucei in our laboratory showed them to possess activities in the low µM range (0.8-8 µM) (scheme 1), and confirmed our initial hypothesis that these compounds could be effective as antiparasitic agents. Parallel screening of these compounds against HeLa cells was in line with published data, with cytotoxicity values in the low µM range. Despite the modest potencies and low SIs for these compounds, the presence of the six-membered endoperoxide ring system and a renewable and ready source of supply of the lead compounds prompted us to explore the structure-activity relationship (SAR) characteristics of merulin core. We therefore undertook a large-scale culture and isolation effort which yielded 415 mg of merulin A, as well as small quantities of merulins B (10 mg) and C (6 mg) for semi-synthetic derivatization.

Because of the importance of artemisinin and other endoperoxide compounds in antimalarial therapy, substantial effort has been applied to determining the mode of action of this compound class. Despite application of a rich array of different approaches, the identification of the mode of action remains an elusive goal. Because of the ambiguity surrounding the molecular target(s), it has also proved difficult to generate clearly defined pharmacophore models for these compound series. Rather than focusing on a pharmacophore-based approach to drive merulin A analogue development, we elected to focus our attention on the improvement of pharmacokinetic (PK) properties to design the analogue series.

Comparison of merulin A to desired drug-like physical properties (Table 2) indicates several physical properties that could be manipulated to generate analogues with more drug-like properties. In particular, the number of rotatable bonds (nRotB), calculated partition coefficient (cLogP), and number of aromatic rings (nArmR) are lower than the mean values for current drugs. Fortunately, due to the low molecular weight (MW) of merulin A (284 amu), it was possible to consider introducing additional structural motifs without surpassing the theoretical optimal MW of 500 amu.

In considering the structure of merulin A it was clear that three positions (carbonyl C8, alpha-carbon C9 and hydroxyl on C3) were best suited to chemical derivatization. Consequently these positions were selected as preliminary chemical handles for expanding the SAR model for the merulin core. Initial attempts to derivatize the carbonyl position using Tebbe olefination, Corey-Chaykovsky epoxidation, Takai iodo olefination, and Baeyer-Villiger oxidation proved unsuccessful. However, treatment of 1 with $LiBH_4$ in THF resulted in diastereospecific reduction of the ketone to the R alcohol (7) as the sole diastereomer. In addition, treatment of 1 with hydroxylamine lead to the formation of oxime 8. Because our initial hypothesis suggested that the endoperoxide was an essential structural feature, we converted merulin to the corresponding diol (9) by opening the epoxide ring under hydrogenation conditions.

Attempts to derivatize the alpha position using a variety of approaches proved problematical, likely due to the small scale (<2 mg) on which these reactions were being attempted. However, derivatization at the alcohol at position C3 was readily accomplished in high yield to afford esters 10 and 11.

Screening of this initial compound series (4-11) revealed a number of SAR features that were crucial to the design of the second-generation library (Scheme 1). As expected, opening of the epoxide ring 9 lead to a complete loss of activity. In addition, reduction of carbonyl also eliminated activity. Interestingly, oxime 8 showed comparable activity to merulin A, which we attribute to the conversion of the oxime back to the original carbonyl species by mild basic hydrolysis in the culture media used for parasite screening. The three compounds in this initial SAR series that possessed structural differences at the secondary alcohol (5, 10, and 11) all displayed similar activities to merulin A, suggesting that this position was suitable for further derivatization, and tolerant of a range of steric and stereoelectronic modifications. However, none of these new derivatives displayed improved potency or selectivity indices over the parent compound. By contrast, merulin C (6) displayed significantly improved activity (0.8 μM), suggesting that the potency of this initial scaffold could be improved by structural modification. Merulin C contains variations at the secondary alcohol, the addition of an α,β-unsaturated carbonyl, and an alternative connectivity for the endoperoxide bridge. This combination of structural variations made it impossible to determine which was responsible for the improvement in activity, however it provided encouragement for further development of this series.

A second-generation library was designed, centered around the derivatization of the secondary alcohol at position C3 in merulin A. This library was designed to improve nRotB, cLogP, and the number of aromatic rings to make these derivatives more drug-like, without surpassing the acceptable MW limit. In particular, the cLogP values for the initial SAR series (Scheme 1) were low (1.37-2.13), compared with the accepted range for drug-like molecules (4-4.5). This value is particularly important for drug leads against trypanosomes, as these parasites contain complex cell membranes and numerous internal vesicles, such as glycosomes, which are potentially valuable drug targets, but which require compounds with the ability to cross multiple membranes.

In order to improve cLogP values, we selected a suite of 20 carboxylic acid building blocks with an array of functionalities including heterocyclic aromatics, basic, aliphatic and halogenated derivatives. These acids were each coupled to merulin A through the formation of ester linkages at position C3, which resulted in a shift to higher clog P values, mostly in the range 4.0-4.5.

Parallel screening of these derivatives against $T.$ $brucei$ and HeLa cells revealed that many of these new analogues had comparable or improved activities compared to merulin A (Table 3). In particular, compounds 12 and 13 showed excellent antiparasitic activities (54 nM and 60 nM respectively).

In addition, cytotoxicity values were typically in the high μM range, with several of the library members having SIs>100. A plot of SI vs. potency against $T.$ $brucei$ (FIG. 2) revealed a positive correlation between potency and selectivity, suggesting that the cytotoxic and antiparasitic activities are biologically independent of one another, and that derivatization can successfully be employed to selectively improve potency while simultaneously abrogating cytotoxicity.

Figure 3:
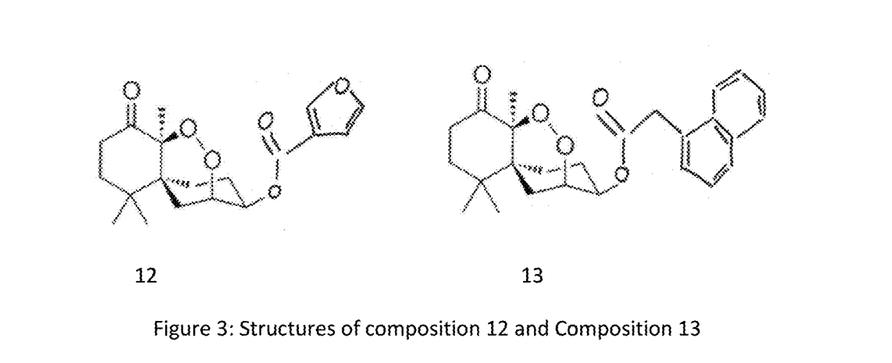
FIG. 3: Structures of Compound 12 and Compound 13.

In order to explore the cumulative effects of varying nRotB, nArmR and cLogP on activity we analyzed this dataset using a four-dimensional plot (FIG. 3), where potency is represented by increasing diameter for each sphere, with the most potent compounds having the largest diameters. This analysis revealed that possession of at least one aromatic ring and at least 3 rotatable bonds were required for activity. In addition, the most potent compounds (12 and 13) possessed clogP values between 3.97 and 5.40, and nRotB values greater than 3.

Compounds with cLogP values greater than 5.4 were less active, suggesting that only a comparatively narrow range of cLogP values are suitable for lead compounds against this target.

In conclusion, we report the semi-synthetic optimization of the merulin class of endoperoxide natural products as development candidates against $T.$ $brucei$, one of the causative agents of African sleeping sickness. We have created a library of 25 merulin analogues using a variety of synthetic approaches, and identified several key physicochemical properties that are important for improving biological potency.

Figure 1:
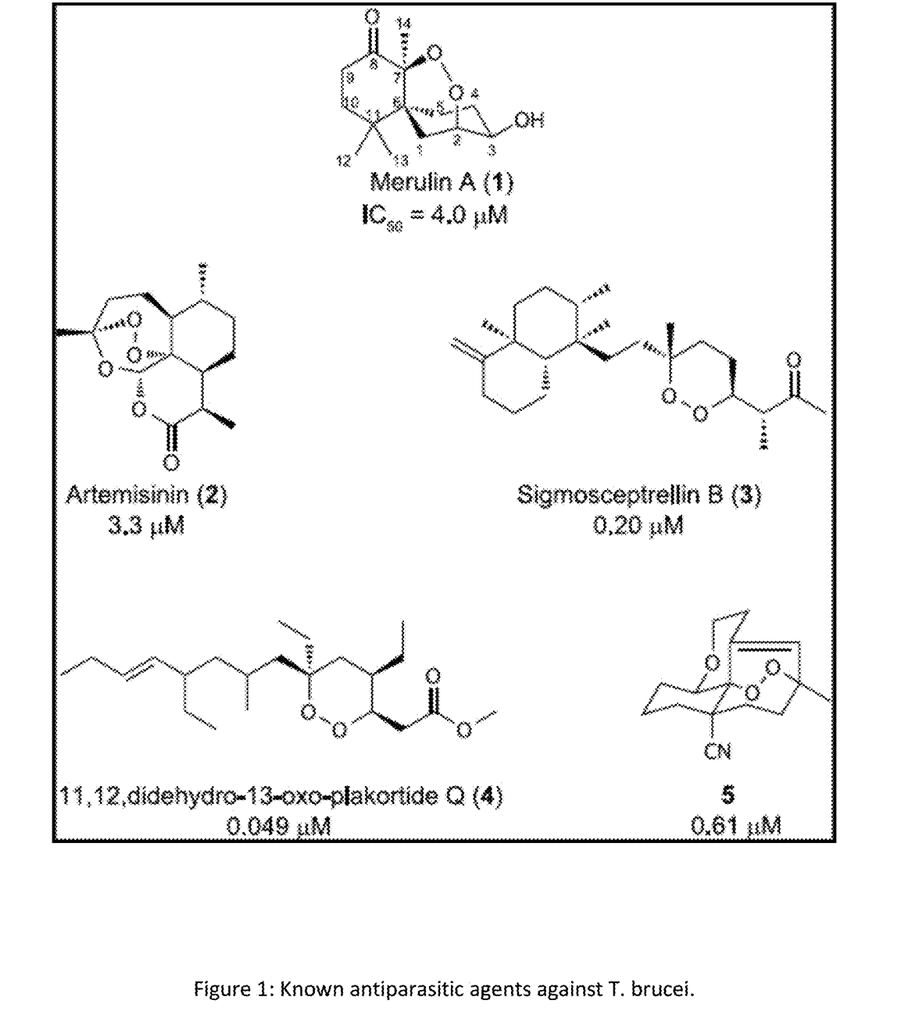
FIG. 1: Known antiparasitic agents against *T. brucei*.
Figure 2:
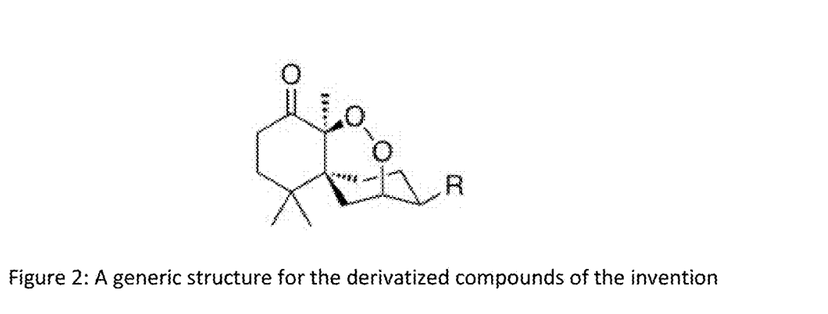
FIG. 2: A generic structure for the derivatized compounds of the invention.

The embodiments include derivatives of the generic structure as shown:

In certain embodiments of this structure, R can be any substituent. In other embodiments it may be selected from an acyl group, an aryl group, a heterocyclic aryl group or a derivatized variant thereof. In other embodiments R may be a cyclic or heterocyclic group or a derivative thereof. In another embodiment R may be selected from the group consisting or —Ra, —CORa, —CONRaRb, —SO2Ra, —COORa, —OCORa, —ORa, —SRa, wherein Ra and Rb are the same or different, are each independently hydrogen or a group optionally further substituted, selected from straight or branched C1-C8 alkyl, C1-C6 alkenyl, C3-C6 alkynyl, C3-C6 cycloalkyl or cycloalkyl C1-C6 alkyl, heterocycloalkyl, or heterocycloalkyl C1 to C6 alkyl, aryl C1 to C6 alkyl, heteroaryl or heteroaryl C1 to C6 alkyl or either Ra and Rb may form an optionally substituted 3 to 10 membered heterocyclyl or heteroaryl, optionally containing up to three additional heteroatoms or heteroaromatic groups, either within ring systems or as aryl substituents, selected from N, O, S, NH. In addition, heterocyclyl or heteroaryl functional groups may be substituted with up to three halogen derivatives, including —F, —Cl, —Br.

Note that all claimed embodiments include the salts of the structures and compounds described, as well as any derivatives, and variants and also metabolic products.

Figure 9:
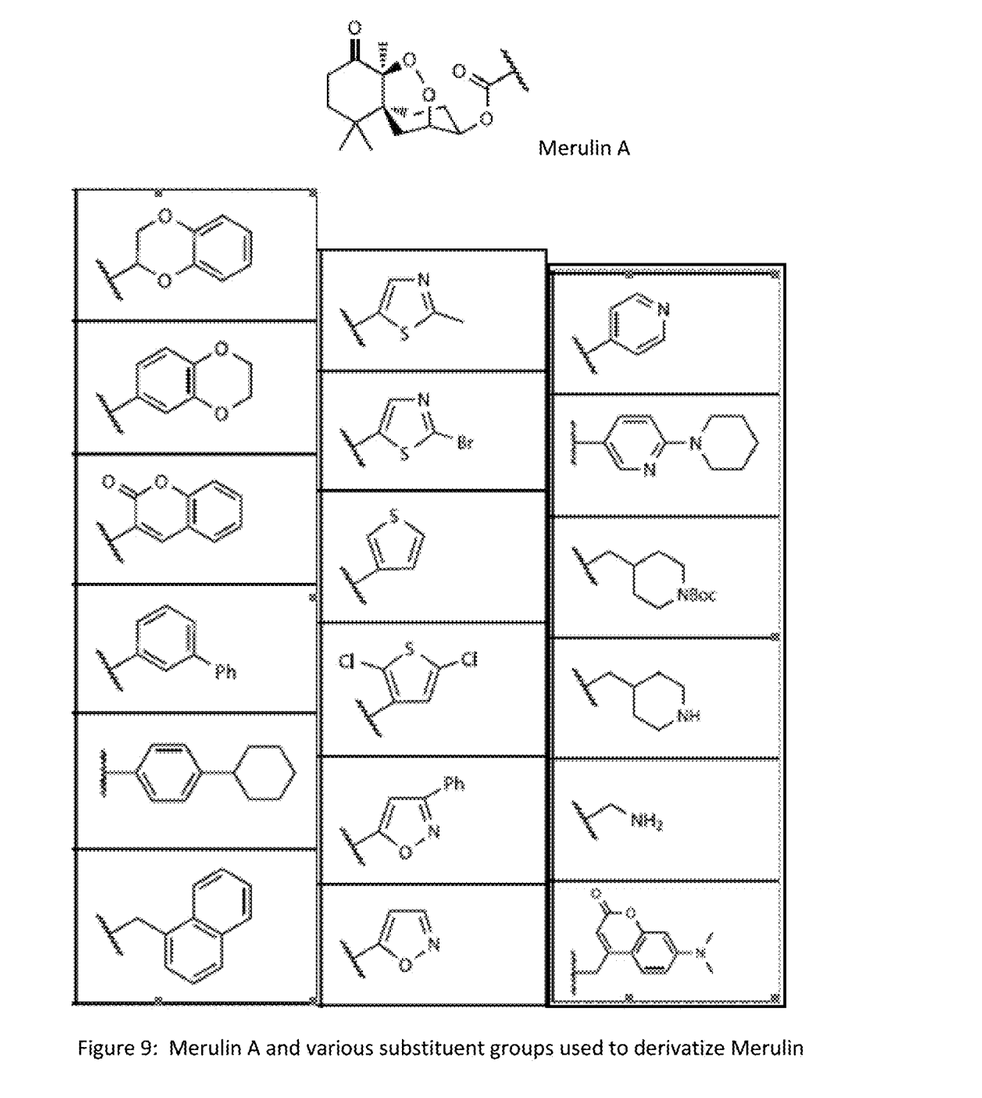
FIG. 9: Various substituent groups used to derivatize Merulin.

Other important exemplary embodiments include the derivatives called "Compound 12" and "Compound 13" and Merulin C and derivatives and analogues of these structures Alternatively the generic structure can be represented by wherein each of R1, R2 and R3 is a hydrogen, and R4 is selected from the substituent structures shown in FIG. 9.

Figure 8:
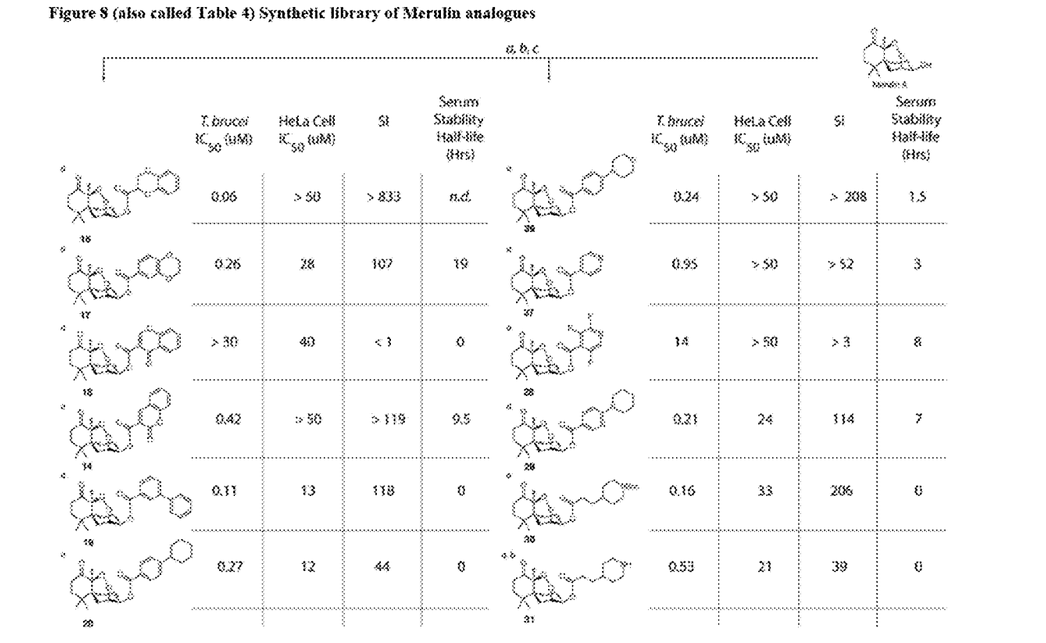
FIG. 8: (also referred to as Table 4): Synthetic library of merulin analogues.

In another embodiment, each of R1, R2 and R3 is a hydrogen, and R4 is selected from the substituent structures shown in FIG. 8.

Or in other embodiments R1, R2 and R3 may independently be any group, the same or different, for example an alkyl or an aryl group, or a hydrogen group, an organic acid, and amine group or a halide or a hydrogen. R4 may be selected from any group, for example, but not exclusively, groups described above for R.

In the process of derivatization used to produce compounds of the invention, R1, R2 and R3 are likely to stay in their natural state and not be changed. This is because the chiral core comes from the fungus from which the natural compounds are derived, and therefore it will be difficult to vary the core which does not vary naturally at these positions. They are C—H bonds, and hard to activate, so it is unlikely that the inventors or any others would actively seek to change these positions.

However, preliminary stability studies have shown that the lead compounds are very easily broken down by liver microsomes, likely through cleavage of the ester group. Therefore the R group (or R4 group) will show considerable variability.

Importantly, the inventors have identified two compounds with low nM antiparasitic activities, and high selectivity indices (12 and 13), and have shown that one of these (12) possesses a half-life greater than 12 hours in our in vitro serum stability assay.

These results have allowed the inventors to go some way towards meeting the TPP requirements of the WHO for new drug leads in this area. These compounds can be produced economically in large quantities via a one step derivatization from the microbial fermentation broth, making these compounds exciting lead candidates for further development.

General Representations Concerning the Disclosure

This specification incorporates by reference all documents referred to herein and all documents filed concurrently with this specification or filed previously in connection with this application, including but not limited to such documents which are open to public inspection with this specification.

It should be noted that although the present disclosure refers frequently to African sleeping sickness, the compounds and methods of the invention are directed towards any disease, particularly parasitic diseases caused by amoeba or protozoa or other eukaryotic organisms. Other diseases against which the compounds and methods of the invention include those pathogens and diseases mentioned in the text book "Parasitic Diseases (5th Edition) by Despommier et al., Apple Trees Productions LLC, Pub., which is hereby incorporated by reference for all purposes. Other diseases against which the compounds and methods of the invention include Amoebiasis, Ascariasis, Babesiosis, Chagas disease, Clonorchiasis, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Lyme disease, Mange, Malaria Metagonimiasis, Myiasis, Onchocerciasis, Pediculosis, Scabies, Schistosomiasis, Strongyloidiasis, Taeniasis (cause of Cysticercosis), Toxocariasis, Toxoplasmosis, Trichinosis, and Trichurias.

Other organisms against which the compounds and methods of the invention may be used, either to prevent or treat a disease, include, for example, the following: *Anisakis*, *Ascaris lumbricoides*, Botfly *Balantidium coli*, Bedbug, Cestoda (tapeworm), Chigger, Hookworm, Liver fluke, *Loa loa*, *Paragonimus* (lung fluke), Pinworm, *Plasmodia* (including falciparum, vivax and ovale), *Schistosoma*, *Strongyloides*, Mites, Tapeworm, *Toxoplasma gondii*, all *Trypanosomes*, Whipworm, *Wuchereria bancrofti*, and *Ixodes pacificus*.

The term "parasite" in this disclosure is used broadly to mean any organism that is known to cause a pathology by infection of an animal subject (host). The term "disease" is used to mean any state of an animal that deviates from normal healthy physiology and that is clinically detectable.

The term "binds" or "binding" in connection with the interaction between a one compound or molecule and another compound or molecule, such as a target and a potential binding compound, indicates that the potential binding compound associates with the target to a statistically significant degree as compared to association with proteins generally. Thus, the term "specific binding" refers to binding between two molecules or compounds that is statistically significantly higher than non-specific binding to another molecule. Preferably a binding compound interacts with a specified target with a dissociation constant ($k_d$) of 1 mM or less, for example 0.1-100 nM. A binding compound can bind with "low affinity", "very low affinity", "extremely low affinity", "moderate affinity", "moderately high affinity", or "high affinity" as described herein. In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity. Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules. In particular embodiments, the greater specificity is at least 2, 3, 4, 5, 8, 10, 50, 100, 200, 400, 500, or 1000-fold greater specificity.

The term substituent refers to an atom or group of atoms substituted in place of a hydrogen atom on the parent molecule.

The term "derivative" or "derivative compound" or "derivatized compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The term "fragment" refers to a part of a larger whole, for example a fragment of a molecule may be any dissociated part of that molecule, regardless of size.

The term "specie" or "group" when used to describe an "R" group in a chemical formula, is used to mean any chemical compound, sub-compound or substituent that may chemically interact with (covalently, ionically or by Van der Waal's forces) another molecule or group such as shown on a chemical formula.

The terms "formulation, "drug formulation or "pharmaceutical formulation," refers to a drug combined with a non-drug such as a carrier material designed not to have a pharmaceutical activity, such as pharmaceutical excipient, filler, or carrier material that may be used to modify or improve the drug release, improve its physical and/or chemical stability, dosage form performance, processing, manufacturing, etc.

When a "terminus" or "terminal group" is discussed as having a substituent, side-chain, group or moiety attached, that substituent, side-chain, group or moiety may equally be present at one or more termini or at side locations along the length of the molecule.

The terms "drug" or "therapeutic agent" mean any substance meant to affect the physiology of a subject. Examples of drugs are described in well known literature references such as the Merck Index and the Physicians Desk Reference.

The term "therapeutically effective amount" means an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

Where substitutions are mentioned, sometimes in connection with variable "R" groups as shown in the figures, the substituent groups may be selected from, for example, the following: hydrogen, hydroxyl, carboxylate, alkane, alkene or alkyne groups, substituted or unsubstituted heteroatom, alkyl, alkenyl, alkanoyl, aryl, aroyl, aralkyl, alkylamino cycloalkyl, heterocycloalkyl, heteroaryl, or halogen, azido, fluorophore or polypeptide. In certain embodiments the substituent group may comprise branched or un-branched C1-C18 alkyl, C1-C18 substituted alkyl, C1-C18 alkenyl, C1-C18 acyl, amino, substituted amino, wherein the alkyl, alkenyl or acyl is linear or branched, and optionally substituted with a hydroxyl, an ester and its derivatives, 5 a carboxyl and its derivatives. In a particular embodiment, Any R group may be a lower hydrocarbon substituted with alkoxy, substituted alkoxy, imidate, arylthio, or (substituted aryl)thio. In other embodiments, Any R group may be a lower alkyl selected from methyl, ethyl, propyl, isopropyl, butyl, isobutyl, terabutyl and pentyl. In other embodiments, Any R group may be a lower alkenyl selected from vinyl, substituted vinyl, ethynyl, or substituted ethynyl. In other embodiments, Any R group may be a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, Any R group may be lower aryl selected from phenyl, p-tolyl, pchlorophenyl, p-aminophenyl, p-nitrophenyl, p-anisyl. In yet other embodiments, Any R group may be a lower aroyl selected from benzoyl and naphthoyl. In other embodiments, Any R group may be a lower aralkyl selected from benzyl, benzhydryl, p-chlorobenzyl, m-chlorobenzyl, p-nitrobenzyl, benzyloxybenzyl, or pentaflourobenzyl. In certain other embodiments, Any R group may be a lower alkylamino is selected from monoalkylamino, monoaralkylamino, dialkylamino, diaralkylamino, and benzylamino.

It should be noted that the invention encompasses compounds, methods and treatments wherein compounds of the invention, and their derivatives and analogues, sub-components and fragments derived therefrom, may be employed to treat any disease of any organism, either animal or plant.

As used in this specification, the singular forms "a", "an", and "the" include plural reference unless the context clearly dictates otherwise. Thus, for example, a reference to "a part" includes a plurality of such parts, and so forth.

The term "comprises" and grammatical equivalents thereof are used in this specification to mean that, in addition to the features specifically identified, other features are optionally present.

A number of references exist that contain relevant subject matter useful in the understanding of the invention. These include: (1) Linington, R G, J Gonzalez, L-D Urena, L I Romero, E Ortega-Barria, W H Gerwick: Venturamides A and B: Antimalarial Constituents of the Panamanian Marine Cyanobacterium *Oscillatoria* sp. J. Nat. Prod. 70, 397-401 (2007); (2) McPhail, K L, J Correa, R G Linington et al.: Antimalarial Linear Lipopeptides from a Panamanian Strain of the Marine Cyanobacterium *Lyngbya majuscula*. J. Nat. Prod. 70, 984-988 (2007); and (3) Balunas, M. J.; Linington, R. G.; Tidgewell, K.; Fenner, A. M.; Urena, L.-D.; Della Togna, G.; Kyle, D. E.; Gerwick, W. H. "Dragonamide E, a Modified Linear Lipopeptide from *Lyngbya majuscula* with Antileishmanial Activity" J. Nat. Prod., 2010, 73, 60; and (4) Sarath P. Gunasekera et al., "Dragonamides C and D, Linear Lipopeptides from the Marine Cyanobacterium Brown *Lyngbya polychroa*" J. Nat. Prod., 2008, 71 (5), pp 887-890 These references and all documents and publications referred to in this disclosure are hereby incorporated by reference, in their entirety, for all purposes.

The entirely of the "definitions" sections of the following applications are hereby incorporated by reference for all purposes: PCT/US10/28071, filed 12-Apr.-2010, and WO2009114325 and US20060281914.

The invention claimed is:

1. A method for producing compounds of the formulae the method comprising esterification of Merulin A.

2. The method of claim 1 wherein the derivatized compound produced by said method is 3. A method of producing compound of formula the method comprising esterification of Merulin A.

* * * * *